United States Patent [19]

Kawai et al.

[11] Patent Number: 5,590,164
[45] Date of Patent: Dec. 31, 1996

[54] METHOD AND APPARATUS FOR X-RAY COMPUTED TOMOGRAPHY

[75] Inventors: Hiroyuki Kawai, Tokyo; Kensuke Sekihara, Musashimurayama; Shinichi Migita, Ryugasaki, all of Japan

[73] Assignee: Hitachi Medical Corporation, Tokyo, Japan

[21] Appl. No.: 456,382

[22] Filed: Jun. 1, 1995

[30] Foreign Application Priority Data

Jun. 28, 1994 [JP] Japan .................................. 6-146332

[51] Int. Cl.$^6$ ............................................... A61B 6/00
[52] U.S. Cl. ............................... 378/4; 364/413.3; 378/19
[58] Field of Search .......................... 364/413.13, 413.16, 364/413.18, 413.19; 378/4, 11, 12, 16, 901, 19

[56] References Cited

U.S. PATENT DOCUMENTS 5,173,852  12/1992  Lonn ................................... 364/431.14
5,469,486  11/1995  Hu et al. ..................................... 378/4

FOREIGN PATENT DOCUMENTS 4231940  8/1992  Japan .

Primary Examiner—Don Wong
Attorney, Agent, or Firm—Antonelli, Terry, Stout & Kraus

[57] ABSTRACT

An X-ray computed tomography apparatus includes a controller for shifting an X-ray focal spot position of an X-ray source, a plurality of first temporary holding devices respectively connected to X-ray detector elements to temporarily hold measured values of X-ray intensity transmitted through an object to be incident on the X-ray detector elements, a switch device for switching over connection between the X-ray detector elements and the first temporary holding devices, a controller for controlling switchover of the switch device, a transfer device for transferring the measured values from the first temporary holding devices to an interpolation calculating device, an interpolation calculating device for performing interpolation calculations on the projection data to generate projection data equivalent to projection data measured by using a measuring system virtually having twice as many X-ray detector elements as the arranged X-ray detector elements, a memory for holding parameters used for calculations in the interpolation calculating device, and an image reconstructor for reconstructing a tomographic image on the basis of the projection data generated by interpolation calculating device.

21 Claims, 13 Drawing Sheets

● MEASURED POINT IN FIRST PROJECTION

○ MEASURED POINT IN SECOND PROJECTION

● MEASURED POINT IN FIRST PROJECTION

○ MEASURED POINT IN SECOND PROJECTION

✕ MEASURED POINT CALCULATED BY INTERPOLATION

METHOD AND APPARATUS FOR X-RAY COMPUTED TOMOGRAPHY

BACKGROUND OF THE INVENTION

The present invention relates to an X-ray computed tomography apparatus for measuring required projection data by using the X-ray and rotating a scanner around an object, in particular to a method and apparatus for X-ray computed tomography capable of providing reconstructed images with high resolution by shifting the position of the X-ray focal spot of an X-ray source with respect to the scanner.

FIG. 2 shows a typical configuration of the conventional X-ray computed tomography apparatus of the third generation. On a scanner 1, Nb X-ray detector elements d0 through d(Nb−1) are disposed on the opposite side of an object 4 from an X-ray source 2. The X-ray source 2 emits an X-ray 5 in a fan beam form. X-ray intensities transmitted through the object 4 are detected by the X-ray detector elements d0 through d(Nb−1) and measured. Data thus measured are called projection data. The projection data are sent to an image reconstructor 7 via a multiplexer 6.

Centering around a center 3 of rotation, the scanner 1 rotates around the object 4 and emits a fan beam 5 to the object 4. The X-ray detector elements d0 through d(Nb−1) measure projection data derived from all directions. On the basis of all projection data thus acquired, the image reconstructor 7 reconstructs the distribution of X-ray attenuation coefficient on a measured cross section of the object 4 as an image. This reconstructed image is displayed on a screen of a display 8. As a calculation method in the image reconstructor 7, the "filtered back-projection method", for example, is known.

As a method for improving the spatial resolution of reconstructed images in X-ray computed tomography apparatuses, a method of obtaining tomographic images while switching over X-ray focal spot position every projection has been proposed (in JP-A-4-231940 and U.S. Pat. No. 5,173,852). Hereafter, this method is called interlacing method.

SUMMARY OF THE INVENTION

FIG. 3 shows the geometrical configuration of the measuring system of FIG. 2 showing a conventional technique.

Herein, an X-ray focal spot 9 on an X-ray source 2 is regarded as a point. If a distance Sod between the X-ray focal spot 9 and a center 3 of rotation is given, the spatial position of the X-ray focal spot 9 at an arbitrary time point in signal measurement is specified by an angle "a" seen from the center 3 of rotation. The spatial position of each of X-ray detector elements d0, d1, . . . , d(Nb−1) on the scanner 1 is specified by an angle "b" seen from the X-ray focal spot 9.

An X-ray fan beam 5 is emitted from the X-ray focal spot 9 located in the position of the angle "a." Considering an X-ray beam 10 incident on an X-ray detector element dj, the X-ray beam 10 can be represented by two parameters, i.e., the angle "a" and the angle "b." This parameter (a, b) is plotted on a coordinate plane. Hereafter, this point is referred to as "measured point" 11. If the geometrical condition of the measuring system is the same, this measured point (a, b) can uniquely specify the X-ray beam 10.

In actual measurement, the measured point (a, b) assumes a discrete value. Therefore, all projection data can be associated with a set of a finite number of measured points. Arrangement of measured points simply represents information concerning the geometrical condition of measurement. If projection data are uniformly measured over the entire circumference, for example, then measured points are located on lattice points arranged at regular intervals having coordinates (a, b).

In the actual X-ray computed tomography apparatus, a certain constant minute time is required for measuring processing of each of individual measured values. During that time as well, the scanner continues to run. Therefore, the value of "a" has a temporal spread instead of a point associated therewith. Furthermore, the value of "b" has a spatial spread corresponding to the aperture of each X-ray detector element instead of one point. Therefore, the above described measured point means a minute area having a spread. Hereafter, description will be given by means of one point representing this area.

In the conventional apparatus for X-ray computed tomography, the spatial resolution of a reconstructed image mainly depends on the arrangement density of the X-ray detector elements in implementation. Therefore, the resolution of the reconstructed image can be improved by increasing the arrangement density of the X-ray detector elements in implementation.

From the reason described herafter, however, increasing the density of arrangement of the X-ray detector elements is not practical.

A first reason is limitation in the implementation technique. At the present time, the X-ray detector elements are arranged with the pitch of approximately 1 mm. Further increasing the density needs extremely strict working accuracy.

A second reason is disadvantage in energy utilization efficiency. For example, it is now assumed that X-ray detector elements are ionization type detector elements. In the case of cell type structure having a plurality of X-ray detector elements partitioned by electrodes, electrodes have some thickness. Even if the arrangement pitch of the X-ray detector elements is reduced, however, the thickness of the electrodes cannot be reduced in proportion thereto. Therefore, the ratio of the effective aperture of the X-ray detector elements to the arrangement pitch is decreased. That is to say, the ratio of X-ray dose contributing to measurement to exposure dose obtained from the X-ray source is decreased. The energy utilization efficiency is thus lowered.

Furthermore, in the conventional measuring system, optimum sampling is not effected and aliasing is caused. That is to say, measurement of intensity of X-ray transmitted through the object of examination is effected discretely. When the sampling pitch is not suitable, therefore, artifacts are caused. Assuming now that the aperture of the X-ray detector elements is Db, projection data measured by this detection system are band limited with a spatial frequency of 1/Db. On the basis of the Nyquist sampling theorem, effect of aliasing can be avoided by effecting sampling with a pitch of Db/2.

In implementation, however, the arrangement pitch of X-ray detector elements is nearly equivalent to the aperture thereof and is equivalent to approximately Db. Therefore, this Nyquist condition is not satisfied.

FIG. 4 is a configuration diagram of an X-ray computed tomography apparatus implementing the interlacing method in a conventional technique. The interlacing method in the conventional technique differs from an X-ray computed tomography apparatus conventionally used heretofore in that an X-ray source 2 having a shiftable X-ray focal spot 9 is used and a controller 12 for controlling the shift of this X-ray focal spot 9 is provided. In the interlacing method using such an apparatus configuration, an imaging method hereafter described is used.

At the time of first measurement of projection data, projection data are measured with the X-ray focal spot located in a first position 9. Subsequently at the time of second measurement of projection data, projection data are measured with the X-ray focal spot located in a second position 9'. In subsequent measurement of projection data, the X-ray focal spot is likewise switched over alternately between the first position 9 and the second position 9' and projection data are measured over the entire circumference.

As shown in FIG. 3, it is now assumed that Sid denotes the distance between the X-ray source and an X-ray detector element, Sod the distance between the X-ray source and the center of rotation, Da the rotation angle of the scanner for each projection, Db the arrangement interval represented by an angle seen from the X-ray focal spot, and d the shift distance of the focal spot. In order to cause interlacing of the first projection and the second projection, the angle Da and the distance d are set as represented by expression (1). By the way, d has a positive value in a direction opposite to the tangential direction of rotation, and s is a constant having a value of ½ or 3⁄2.

$$Da = \frac{s \cdot Sid \cdot Db}{Sod} \quad (1)$$

$$d = s \cdot Sid \cdot Db \frac{Sod}{Sid - Sod}$$

FIG. 5 shows an arrangement of measured points according to the interlacing method shown in FIG. 4.

If the angle Da is set as represented by expression (1), the position of the X-ray detector elements is displaced by a distance equivalent to Db/2 or 3Db/2 at the time of a first projection as compared with the position at the time of a second projection.

If the distance d is set as represented by expression (1), the position of the X-ray focal spot at the time of the first projection and the position of the X-ray focal spot at the time of the second projection overlap each other. As a result, the first projection and the second projection are interlaced, and a higher resolution satisfying Nyquist condition can be achieved.

Representing this by using measured points facilitates understanding. FIG. 5 shows the arrangement of measured points obtained when measurement is effected by using the interlacing method with s=3⁄2.

In FIG. 5, measured points in a single projection measured with the X-ray focal spot 9 located in the first position are represented by closed circles arranged on a straight line in direction b. Likewise, measured points in a single projection measured with the X-ray focal spot 9' located in the second position are represented by open circles arranged on a straight line in direction b. The position of the X-ray focal spot 9' in the first projection is the same as that of the X-ray focal spot 9 in the second projection. Therefore, those measured points are arranged on the same line in direction b at intervals of 2Da every two projections.

As described above, measured points in a projection with the X-ray focal spot 9 located in the first position are represented by closed circles. Likewise, measured points in a projection measured with the X-ray focal spot 9' located in the second position are represented by open circles. Therefore, combining measured points in the first projection with measured points in the second projection yields a virtual arrangement of measured points corresponding to the case where measurement is effected by using X-ray detector elements having a doubled arrangement density. Furthermore, since the sampling pitch is Db/2 while the aperture of the X-ray detector elements is Db, the Nyquist condition is also satisfied.

If reconstruction is effected on the basis of projection data thus obtained by combination, a reconstructed image having a high resolution is obtained.

However, the above described conventional interlacing method has a problem of design cost (a first problem), a problem concerning X-ray beam interlacing (a second problem), and a problem concerning measuring timing (a third problem). Hereafter, these problems will be described in order.

First of all, the first problem will now be described. For implementing the interlacing method, such a geometrical configuration that the measuring system satisfies expression (1) is needed. This imposes a strong restriction on design of the apparatus. For implementing the interlacing method, therefore, the apparatus must be subjected to significant redesign.

The second problem will now be described. Even if the measuring system satisfies the geometrical condition, the first projection and the second projection are not interlaced ideally, resulting in the second problem. Considering the X-ray beam passing the vicinity of the center of rotation, the first projection and the second projection are in the interlacing relation according to the condition of expression (1).

That is to say, measured points in the first projection and measured points in the second projection are arranged at regular intervals with a pitch of Db/2 as shown in FIG. 5. As the location moves to a peripheral part, this relation is not satisfied and the measured points in the first projection and the measured points in the second projection are not arranged at regular intervals. This results in a problem that artifacts are caused on the reconstructed image.

A third problem more firmly based upon the principle will now be described. While the X-ray computed tomography apparatus has several hundred X-ray detector elements, only several interfaces are prepared in the image reconstructor. Therefore, several hundred measured data cannot be simultaneously transferred to the image reconstructor. Thus connection between them is switched over by using a multiplexer, and measured data are successively transferred every X-ray detector element. As a result, measuring timing is displaced from detector element to detector element.

It is now assumed that the time required for measurement of one projection is Tp and the time required for each X-ray detector element to measure the intensity of the incident X-ray is Td (0<Td<Tp). FIG. 6 shows the timing chart of measurement in the conventional technique. As shown in this timing chart, measuring time periods needed by X-ray detector elements (i.e., integration time periods of X-ray dose incident upon X-ray detector elements) overlap each other. Throughout all of the measuring time periods, therefore, there is no instant during which any X-ray detector element is not measuring.

In the interlacing method, the X-ray focal spot position must be switched over for every projection, i.e., at intervals of the time Tp required for measurement. No matter how this timing is adjusted, however, switchover of the X-ray focal spot position occurs during the measuring time period for most X-ray detector elements. As a consequence of such inconsistency in projection data, artifacts are generated on the reconstructed image. Since such a problem is caused because of dense measuring timing, it can be avoided by effecting measurement with sparser timing. For example, if the value of the time period Tp required for measurement of one projection is made sufficiently larger than the time period Td required for each X-ray detector element to effect measurement, an interval during which any X-ray detector element does not effect measurement is generated for every projection. By effecting switchover of the X-ray focal spot position during this interval, the above described problem can be avoided.

However, this solution prolongs the dead time and poses a problem in time utilization efficiency. For increasing the X-ray dose included in the exposure from the X-ray source and effectively contributing to measurement and thereby increasing the signal-to-noise ratio without unnecessarily prolonging the measuring time, the measuring time period Td of each X-ray detector element should be as close to the time period Tp required for a single projection as possible. On the assumption that a conventional measured data transfer mechanism is used, the interlacing method cannot be thus implemented without decreasing the time utilization efficiency.

An object of the present invention is to provide a method and apparatus for X-ray computed tomography capable of solving the above described first to third problems of the conventional technique, implementing a higher resolution of the reconstructed image without limiting the degree of freedom on design, obtaining projection data with an ideal sampling pitch even in a peripheral part remote from the center of rotation, effecting measurement on the assumption that the conventional measured data transfer mechanism is used, and executing measurement satisfying the Nyquist condition without lowering the time utilization efficiency.

In accordance with the present invention, the X-ray computed tomography apparatus includes an X-ray source, a device for effecting control to shift the X-ray focal spot position of the X-ray source, integrators for respective X-ray detector elements, a switchover device, and a controller of the switchover device, a device for performing interpolation calculations of derived projection data, and a device for holding parameters required for interpolation calculations. The X-ray focal spot position is switched over alternately between a first position and a second position per projection. Switchover of connection between each X-ray detector element and integrators is effected by a switchover device. In a device for performing interpolation calculations on the basis of obtained projection data, projection data corresponding to projection data obtained by a virtual apparatus having a doubled arrangement density of X-ray detector elements are generated.

In accordance with the present invention, the above described first problem is solved by performing calculations to derive an arrangement of measured points corresponding to projection data obtained by actual measurement and by performing interpolation calculations on the basis of the information to derive projection data located on measured points having a doubled density in a b direction.

An X-ray computed tomography apparatus according to the present invention has a memory for holding parameters required for the interpolation calculations and an interpolation calculating device. The parameters are calculated on the basis of the arrangement of measured points based upon actual measurement and positional relations of the arrangement of measured points having a doubled density in the b direction.

Information of the arrangement of derived measured points, or parameters calculated on the basis thereof and used for interpolation are held in the memory. By using the information held in the memory, interpolation calculations are performed on projection data derived by measurement to obtain corrected projection data. By such interpolation calculations, projection data having an ideal arrangement of measured points are generated. Therefore, the above described second problem is also solved simultaneously.

In accordance with the present invention, a plurality of devices for temporarily holding measured values are prepared for each X-ray detector element, in order to solve the above described third problem. In synchronism with switchover of the X-ray focal spot position, switchover is effected on connection between each X-ray detector element and a device for temporarily holding a measured value or connection between a device for temporarily holding a measured value and another device for temporarily holding a measured value. Thus measurement of projection data is effected.

An X-ray computed tomography apparatus according to the present invention has a switchover device for effecting this switchover and a switchover controller.

In the present invention, reconstruction calculations are not performed on the basis of projection data themselves obtained by actual measurement, but projection data on the arrangement of measured points strictly requested in reconstruction calculations are generated by interpolation. Therefore, flexibility is obtained in the geometric configuration of the measuring system.

Furthermore, projection data having an ideal arrangement of measured points even in the peripheral part remote from the center of rotation are generated by interpolation calculations. Therefore, occurrence of artifacts which would be otherwise caused by deviation of the arrangement of measured points can be avoided.

Since devices for temporarily holding a measured value is connected to each X-ray detector element, measurement to be effected by X-ray detector elements and data transfer to an image reconstructor can be performed independently. Synchronization of measuring timing and successive transfer of measured data can thus be reconciled.

As heretofore described, the present invention makes it possible to obtain projection data having an ideal sampling pitch even in the peripheral part remote from the center of rotation and avoid occurrence of artifacts which would be otherwise caused by deviation of the sampling pitch. Furthermore, measurement satisfying the Nyquist condition can be effected without causing dead time and without lowering the time utilization efficiency on the premise that the conventional measured data transfer mechanism is used.

DESCRIPTION OF THE PREFERRED EMBODIMENTS

Hereafter, embodiments of the present invention will be described in detail by referring to drawing.

Figure 1:
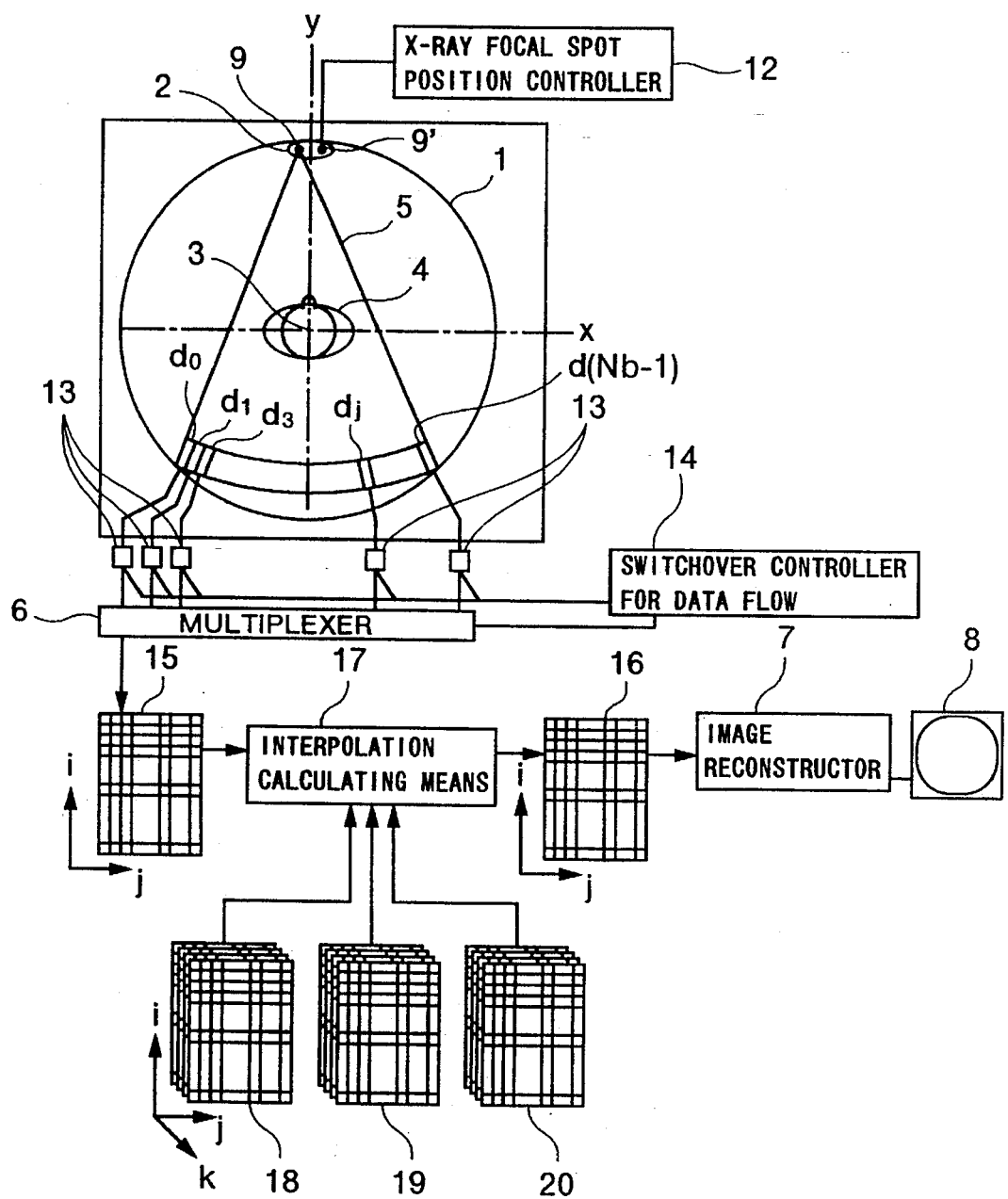
FIG. 1 is a configuration diagram of an X-ray computed tomography apparatus showing a first embodiment of the present invention.
Figure 2:
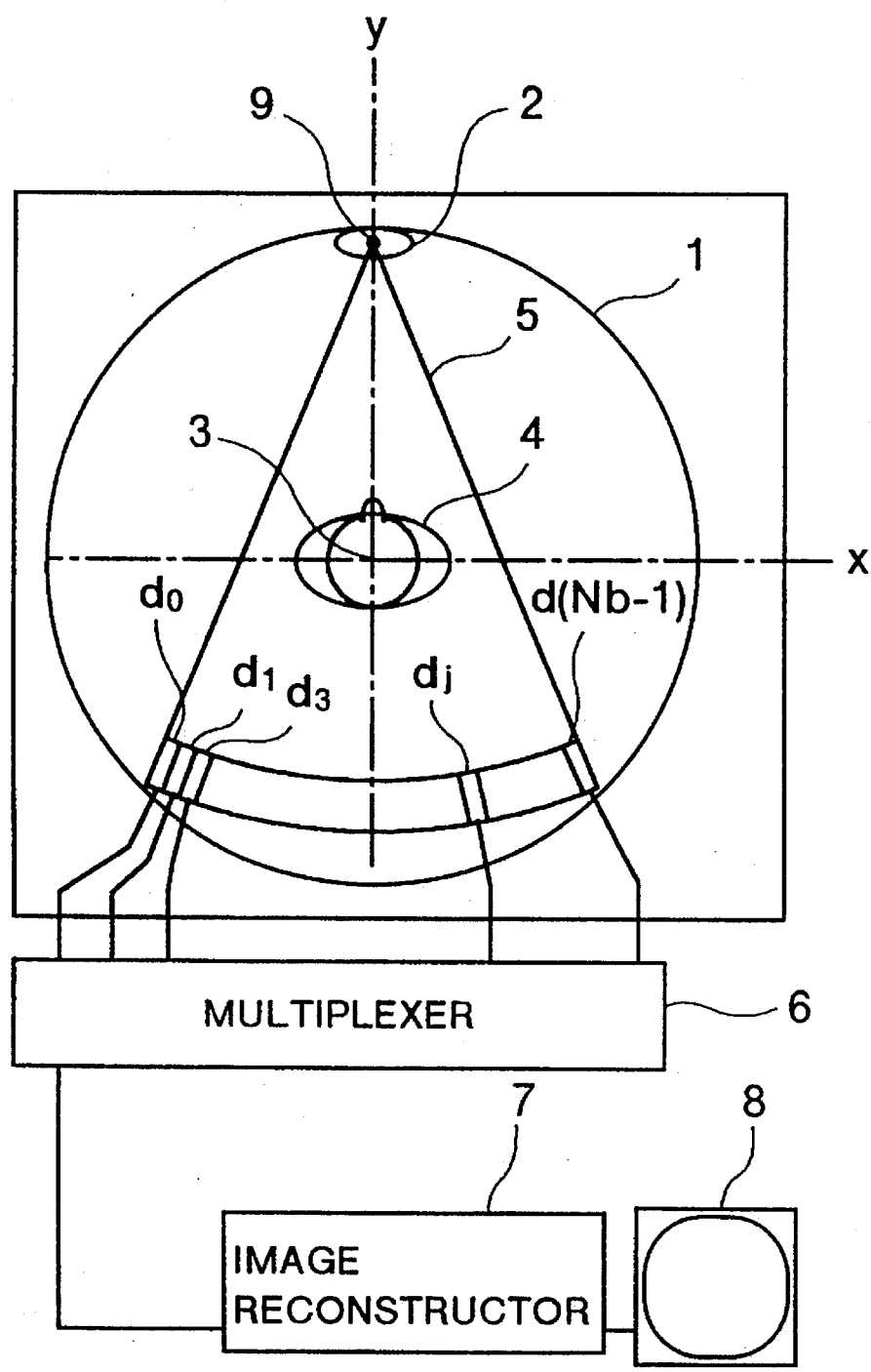
FIG. 2 is a configuration diagram of a conventional X-ray computed tomography apparatus.
Figure 3:
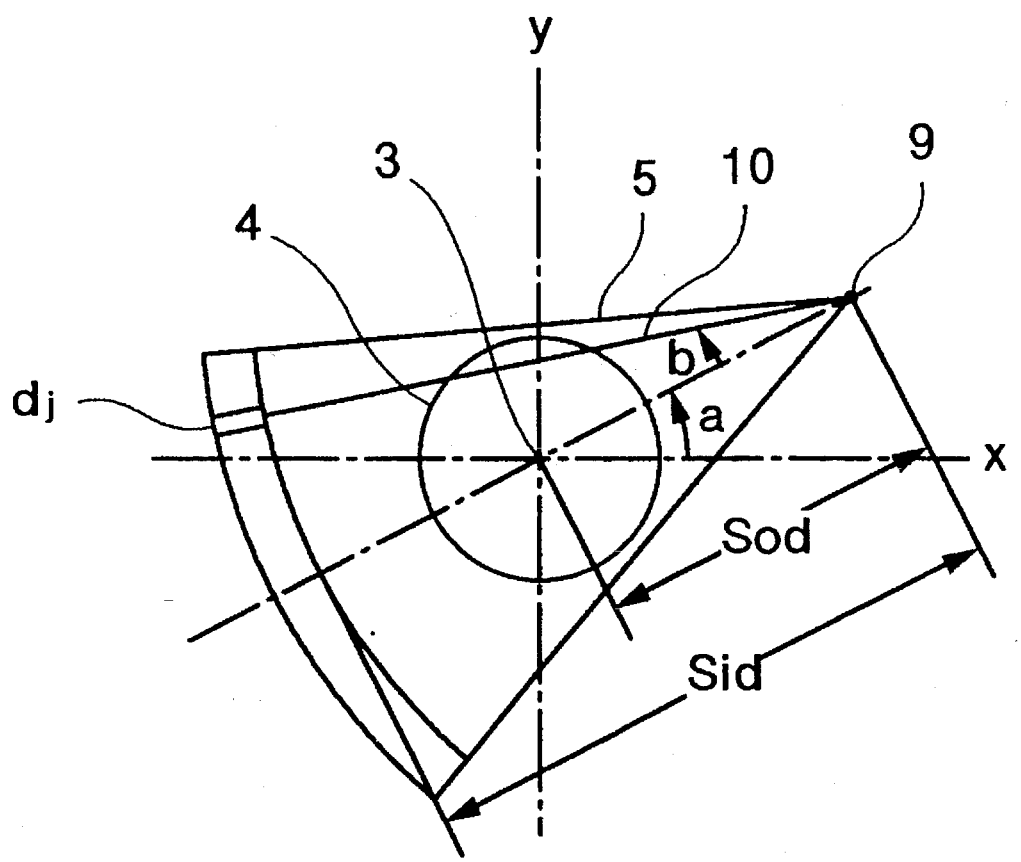
FIG. 3 is a diagram showing the geometric relation of a measuring system of a conventional X-ray computed tomography apparatus.
Figure 4:
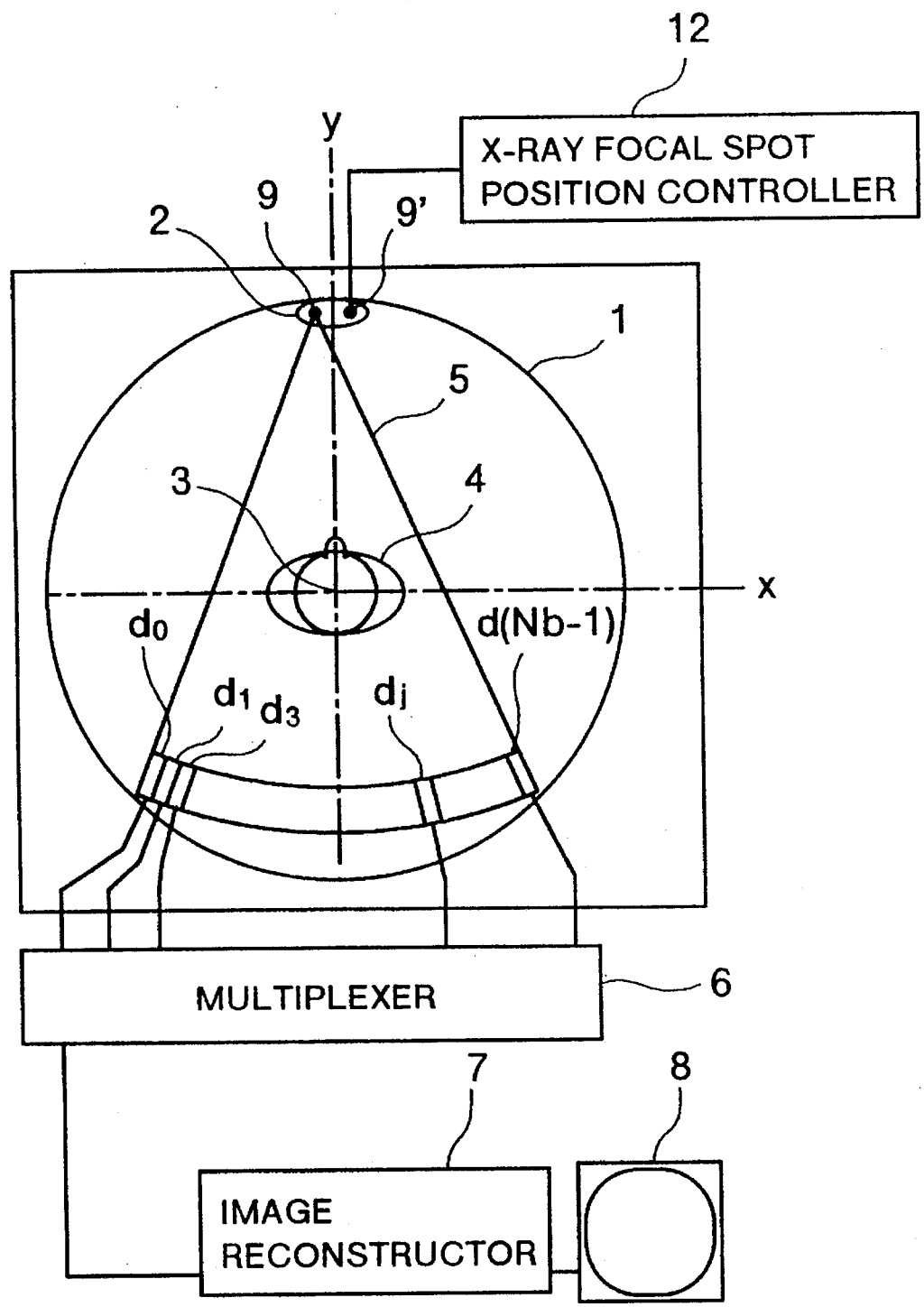
FIG. 4 is a diagram showing an X-ray computed tomography apparatus implementing a conventional interlacing method.
Figure 5:
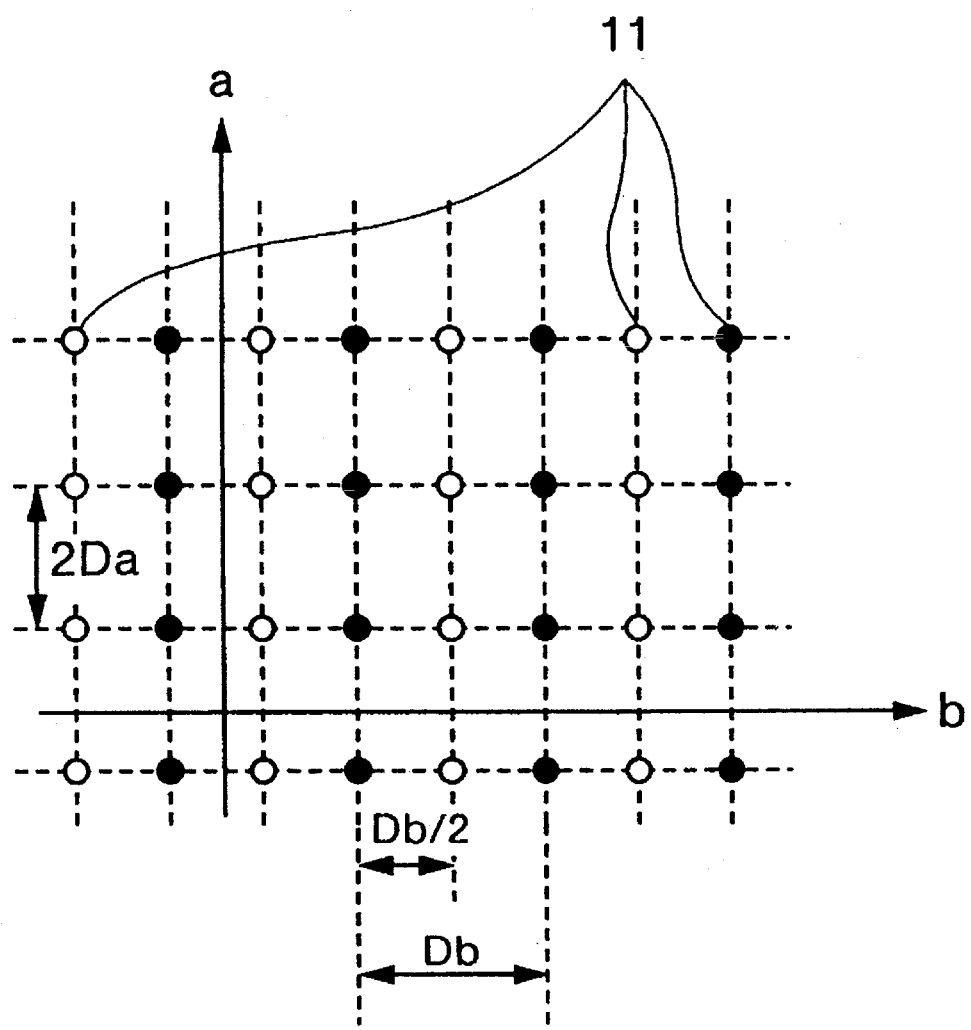
FIG. 5 is a diagram showing arrangement of measured points in the conventional interlacing method.
Figure 6:
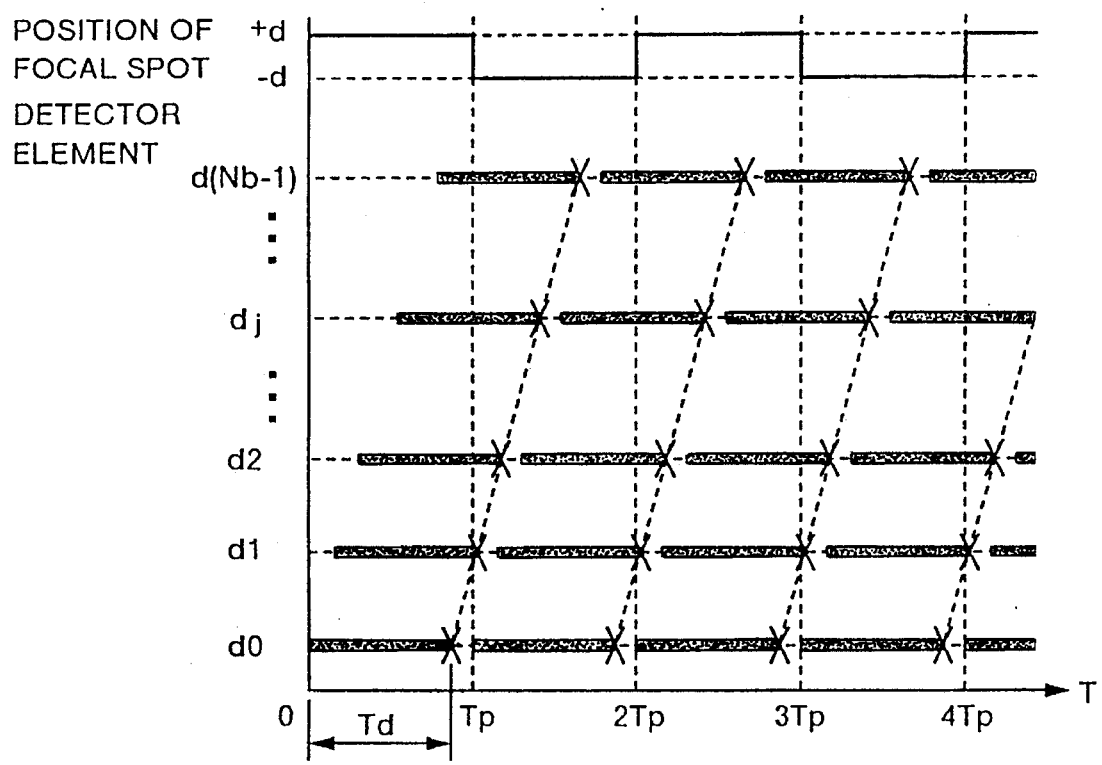
FIG. 6 is a timing chart of measurement showing the integration periods of incident X-ray intensity and timing of data transfer effected by a multiplexer in the conventional apparatus.

FIG. 1 is a configuration diagram of an X-ray computed tomography apparatus showing a first embodiment of the present invention.

In FIG. 1, Nb X-ray detector elements d0 through d(Nb−1) are disposed on the opposite side of an object 4 from an X-ray source 2 on a scanner 1.

In this X-ray source 2, positions of the X-ray focal spots 9 and 9' can be shifted. A controller 12 for controlling the shift of positions of the X-ray focal spots 9 and 9' is provided. The X-ray focal spots 9 and 9' emit an X-ray 5 in a fan beam form. The X-ray intensity transmitted through the object 4 is measured by the X-ray detector elements d0 through d(Nb−1). Hereafter, measured data are referred to as projection data.

The X-ray detector elements d0 through d(Nb−1) are connected to respective devices 13 for holding data temporarily. Projection data held temporarily in these holding devices 13 are passed through a multiplexer 6 with specific timing and transferred to an image reconstructor 7 via memories 15 and 16 and an interpolation calculating device 17. Timing of data transfer from the X-ray detector elements d0 through d(Nb−1) to the temporary data holding devices 13, timing of data transfer from the temporary data holding devices 13 to the multiplexer 6, and timing of data transfer from the multiplexer 6 to the memory 15 are controlled by a switchover controller 14 for data flow. Centering around a center 3 of rotation, the scanner 1 revolves round the object 4 and measures projection data continuously from all directions.

All of projection data thus acquired and subjected to basic processing such as calibration are temporarily held in the memory 15 for measured projection data. The projection data held in the memory 15 are read out and thereafter transferred to the interpolation calculating device 17. In the interpolation calculating device 17, interpolation calculations are performed on all of the projection data and projection data corresponding to projection data obtained by an X-ray computed tomography apparatus virtually doubled in number of X-ray detector elements are generated. The generated projection data are held in the memory 16 for corrected projection data. On the basis of information concerning positions of the X-ray focal spots 9 and 9' at the time of measurement and positions of the X-ray detector elements d0 through d(Nb−1), parameters required for this interpolation are calculated beforehand. The parameters thus calculated are formed on tables 18, 19 and 20, and then held in data storage media such as read only memories or magnetic disks.

Then the projection data read out from the memory 16 are transferred to the image reconstructor 7. In the image reconstructor 7, distribution of X-ray attenuation coefficient on a measured cross section of the object 4 is reconstructed as an image on the basis of the corrected projection data. This reconstructed image is displayed on a screen of a display 8. As this reconstruction calculation, the "filtered back-projection method", for example, is known.

Figure 7:
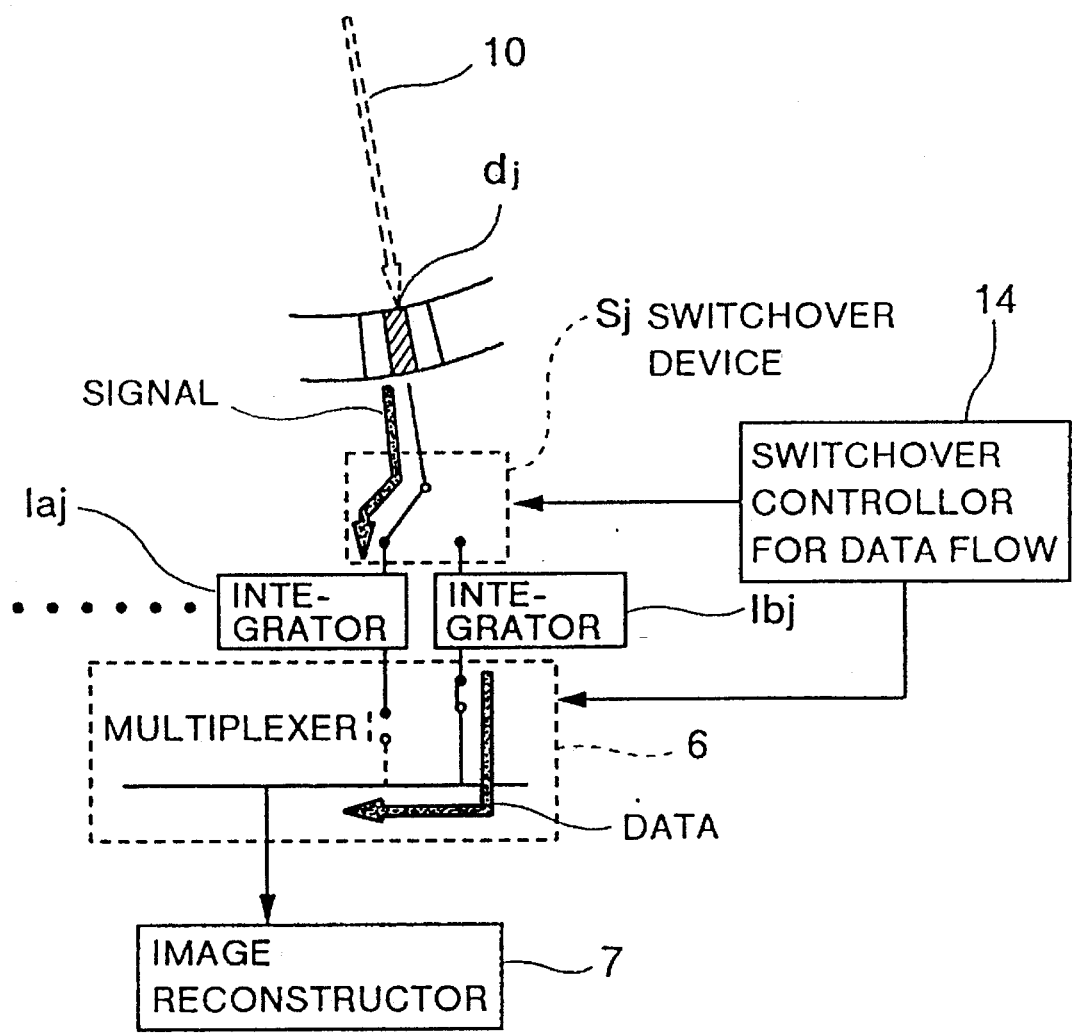
FIG. 7 is a principal part configuration diagram of a measuring system of an X-ray computed tomography apparatus showing a first embodiment of the present invention.

FIG. 7 is a configuration diagram of a principal part of an X-ray computed tomography apparatus showing a first embodiment of the present invention.

By providing X-ray detector elements d0 through d(Nb−1), devices 13 for holding data temporarily, a multiplexer 6, and a switchover controller 14 in the case of FIG. 7, measurement effected by the X-ray detector elements can be separated from transfer of data to the image reconstructor.

In order to avoid complexity, description will now be given as to an X-ray detector element dj. As a matter of fact, the configuration hereafter described applies to all of the X-ray detector elements d0 through d(Nb−1).

For the X-ray detector element dj, two integrators Iaj and Ibj are prepared. Herein, integrators Iaj (j=0, 1, 2, ..., Nb−1) are referred to as first group, and integrators Ibj (j=0, 1, 2, ..., Nb−1) are referred to as second group. Between the X-ray detector element dj and the integrators Iaj and Ibj, a switchover device Sj is interposed. Connection between the X-ray detector element dj and the integrators Iaj and Ibj is controlled by the switchover controller 14 according to focal spot position switchover timing. Outputs of the integrators Iaj and Ibj are transferred to the image reconstructor 7 via the multiplexer 6 under the control of the switchover controller 14.

Figure 8:
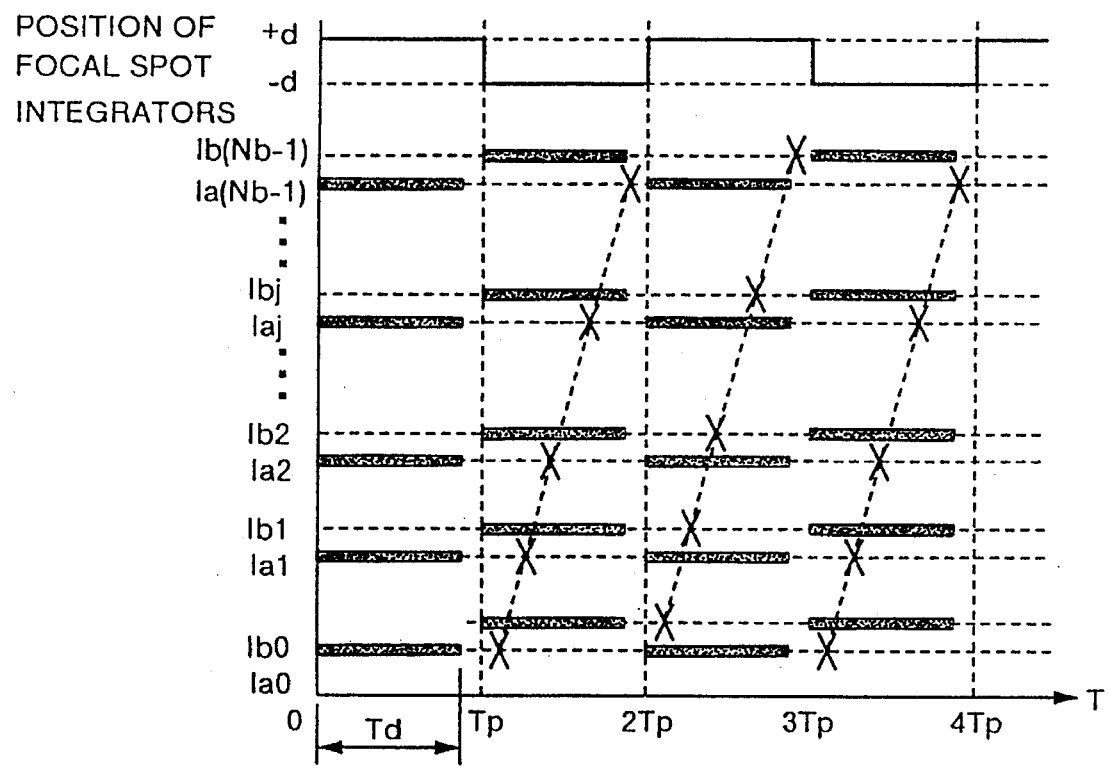
FIG. 8 is a timing chart of the measuring system in the first embodiment.

FIG. 8 is a timing chart of measuring operation conducted by the first embodiment of FIG. 7.

In FIG. 8, Ia0 through Ia(Nb−1) and Ib0 through Ib(Nb−1) denote integrators of the first group and the second group, respectively.

The X-ray focal spot is shifted, and the X-ray is emitted in a first position 9. And i-th projection data is measured. During the time period required for this measurement (data acquisition period) Td, the output of the X-ray detector element dj is sent to the integrator Iaj of the first group by the switchover device Sj. That is to say, the integrators of the first group measures projection data (i.e., acquires data) when the X-ray focal spot is in the first position 9. On the other hand, (i−1)-th projection data, i.e., projection data obtained when the X-ray focal spot is in the second position 9' is stored in the integrators of the second group. While the input X-ray intensity is being integrated by the integrators of the first group, therefore, data are successively transferred from the integrators of the second group to the image reconstructor 7 via the multiplexer 6.

At the time of measurement of (i+1)-th projection data, the integrators of the first group exchange roles with the integrators of the second group and similar operation is conducted.

First of all, switchover of the X-ray focal spot position is effected in the X-ray source 2. The X-ray focal spot is shifted, and the X-ray is emitted in a second position 9'. And (i+1)-th projection data is measured. During the time period Td required for this measurement, the output of the X-ray detector element dj is sent to the integrator Ibj of the second group by the switchover device Sj. That is to say, the integrators of the second group measures projection data (i.e., acquires data) when the X-ray focal spot is in the second position 9'. On the other hand, i-th projection data, i.e., projection data obtained when the X-ray focal spot is in the first position 9 is stored in the integrators of the first group. While the input X-ray intensity is being integrated by integrators of the second group, therefore, data are successively transferred from the integrators of the first group to the image reconstructor 7 via the multiplexer 6.

The measurement heretofore described is repeated over the entire circumference.

The prime object of adopting the apparatus configuration and measuring method heretofore described is to set timing for switching over the X-ray focal spot position without lowering time utilization efficiency. By providing duplicate integrators, measurement of projection data and transfer of measured data to the image reconstructor can be effected separately and independently. Therefore, synchronization of measurement of projection data in all X-ray detector elements and successive transfer of measured data to the image reconstructor can be realized without incurring dead time and without lowering time utilization efficiency. The above described problem can be solved.

Figure 9:
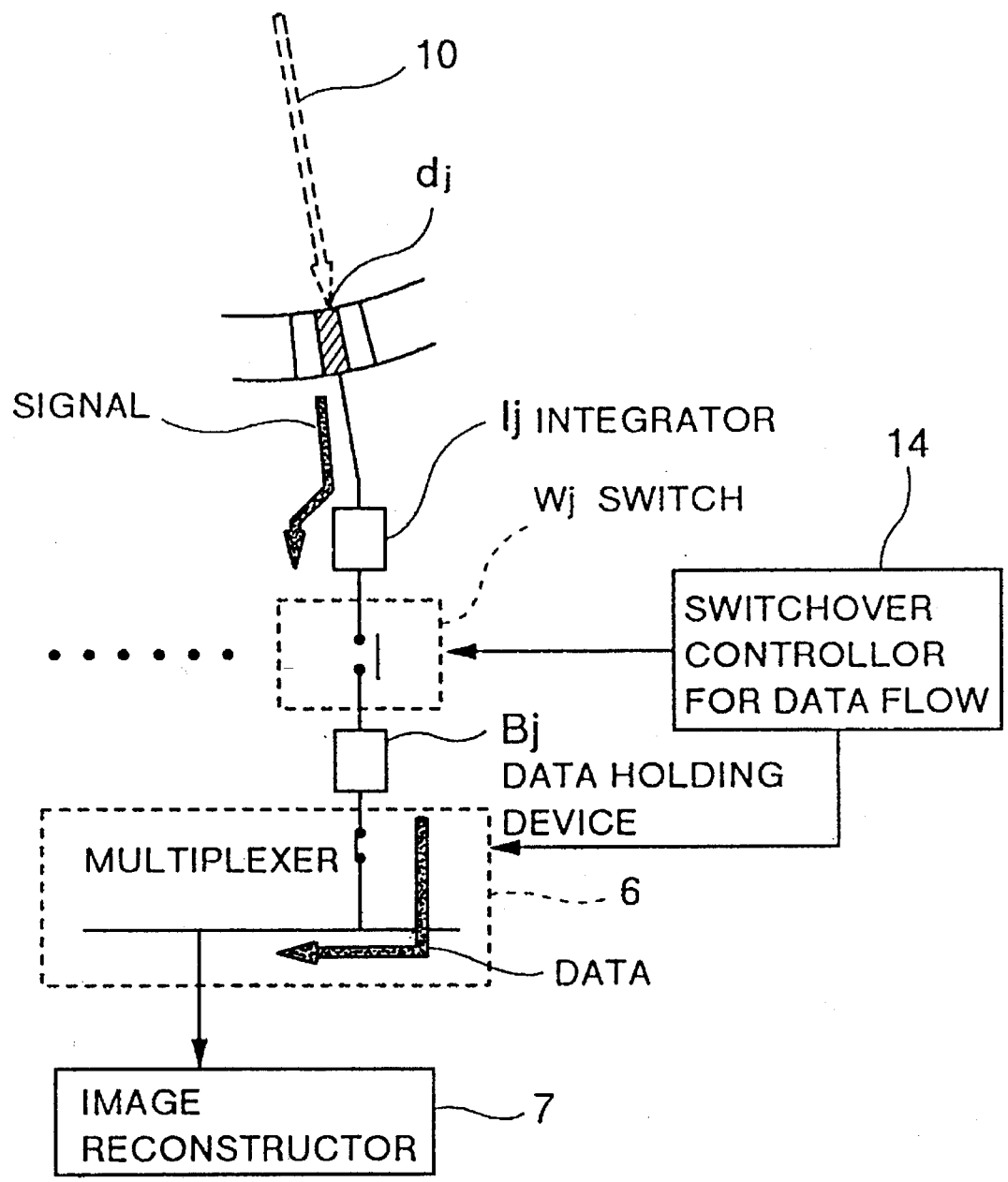
FIG. 9 is a principal part configuration diagram of a measuring system of an X-ray computed tomography apparatus showing a second embodiment of the present invention.

FIG. 9 is a configuration diagram of a principal part of an X-ray computed tomography apparatus showing a second embodiment of the present invention.

In FIG. 9, a function similar to that of FIG. 7 is implemented by using a different configuration.

FIG. 9 shows the schematic configuration of X-ray detector elements d0 through d(Nb−1), an integrator Ij and a second data holding device Bj functioning as the temporary data holding device 13, a multiplexer 6, a switchover controller 14 for data flow, and a switch Wj.

For an X-ray detector element dj, the integrator Ij and the second data holding circuit Bj are prepared. The second data holding circuit Bj is used to temporarily hold measured data. The output of the X-ray detector element dj is integrated in the integrator Ij during the measuring time Td. The integrator Ij is connected to or disconnected from the second data holding circuit Bj by the switch Wj. The data held in the second data holding circuit Bj is transferred to the image reconstructor 7 via the multiplexer 6. Turning the switch Wj on/off and data transfer are controlled by the data flow switchover controller 14 according to switchover timing of focal spot position.

Figure 10:
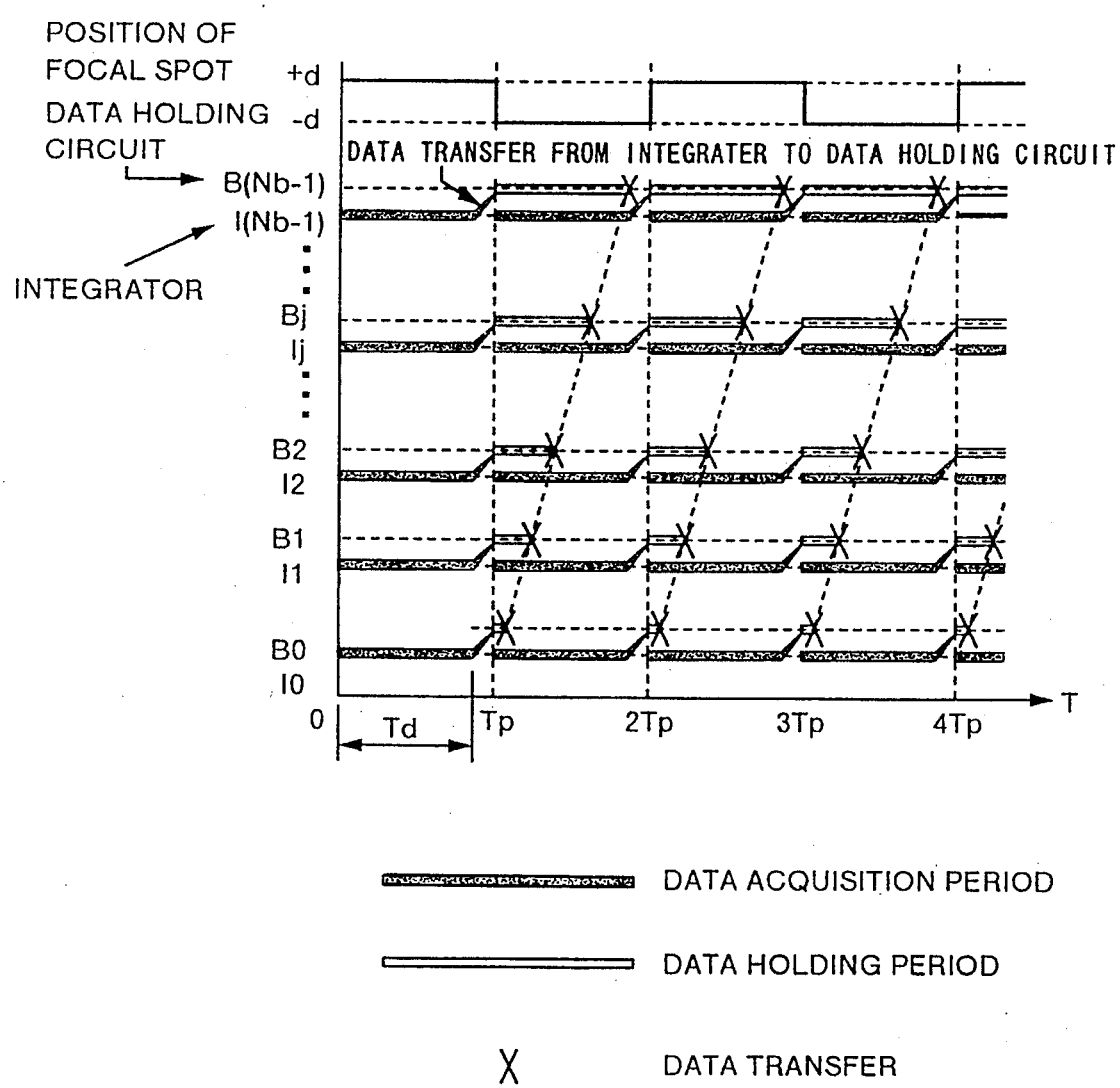
FIG. 10 is a timing chart of the measuring system in the second embodiment.

FIG. 10 is a timing chart of measuring operation in the second embodiment shown in FIG. 9.

In FIG. 10, I0 through Ij denote integrators and B0 through Bj denote second data holding circuits.

The X-ray focal spot is shifted, and the X-ray is emitted in a first position 9. And i-th projection data is measured. During the time period required for this measurement (data acquisition period) Td, the output of the X-ray detector element dj is integrated in the integrator Ij. During this time, the integrator Ij is disconnected from the second data holding circuit Bj by the switch Wj. In the second data holding circuit Bj, (i−1)-th projection data, i.e., projection data obtained when the X-ray focal spot is in the second position 9' is stored. While the input X-ray intensity is being integrated by the integrator Ij, therefore, data are successively transferred from the second data holding circuits Bj to the image reconstructor 7 via the multiplexer 6. Data of the second data holding cirucits Bj completed in data transfer are erased.

Then the switch Wj is closed. The integral value of the i-th projection data is transferred from the integrator Ij to the second data holding circuit Bj. At the time when this data transfer has been effected, the switch Wj is opened again and the integrator Ij is diconnected from the second data holding circuit Bj. During this time, switchover of the X-ray focal spot position is effected.

At the time of measurement of (i+1)-th projection data as well, operation similar to the above described operation is conducted. The X-ray focal spot is shifted, and the X-ray is emitted in a second position 9'. And (i+1)-th projection data is measured. During the time period Td required for this measurement, the output of the X-ray detector element dj is integrated in the integrator Ij. During this time, the integrator Ij is disconnected from the second data holding circuit Bj by the switch Wj. In the second data holding circuit Bj, the i-th projection data, i.e., projection data obtained when the X-ray focal spot is in the first position 9 is stored. While the input X-ray intensity is being integrated by the integrator Ij, therefore, data are successively transferred from the second data holding circuits Bj to the image reconstructor 7 via the multiplexer 6. Data of the second data holding cirucits Bj completed in data transfer are erased.

Then the switch Wj is closed. The integral value of the i-th projection data is transferred from the integrator Ij to the second data holding circuit Bj. At the time when this data transfer has been effected, the switch Wj is opened again and the integrator Ij is diconnected from the second data holding circuit Bj.

Measuring processing heretofore described is repeated over the entire circumference.

In the second embodiment as well, the prime object of adopting the apparatus configuration and measuring method heretofore described is to set timing for switching over the X-ray focal spot position without incurring dead time and without lowering time utilization efficiency. By providing the second data holding circuit between the integrator and the multiplexer, measurement of projection data and transfer of measured data to the image reconstructor can be effected separately. Therefore, synchronization of measurement of projection data in all X-ray detector elements and successive transfer of measured data to the image reconstructor can be realized efficiently. The above described problem can be thus solved.

In the first embodiment, it is necessary to double the number of channels of the input side of the multiplexer as compared with the conventional technique or increase the number of multiplexers twice. In the seond embodiment, however, the multiplexer identical in number of channels or number of multiplexers with the conventional technique can be used.

In the first and second embodiments, the object of the present invention is achieved by duplicating temporary data holding devices, i.e., preparing two integrators, or an integrator and a second data holding circuit. Not only such an embodiment having duplicated temporary data holding devices, but also an embodiment having a plurality of temporary data holding devices is conceivable. In the case a plurality of temporary data holding devices are provided, the flexibility is advantageously increased as to timing setting of data measurement and timing setting of data transfer. As a matter of fact, it is necessary in this case to provide switchover controllers for data flow associated with a plurality of temporary data holding devices.

Means and the method for processing data will now be described.

Figure 11:
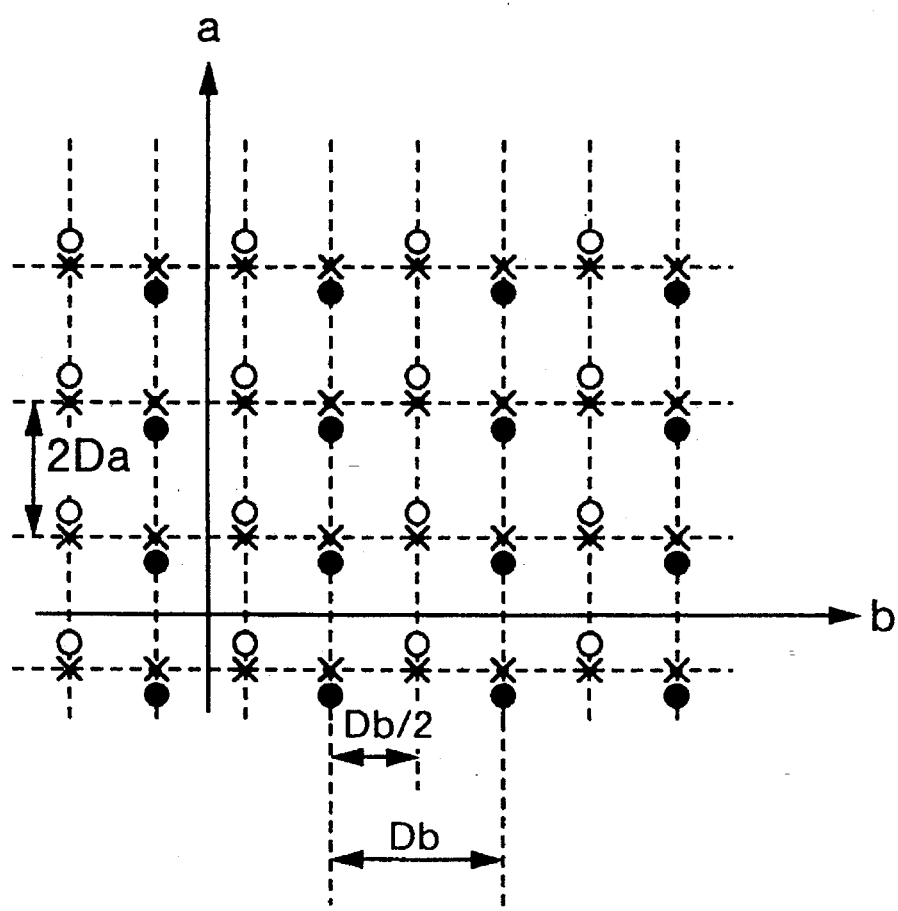
FIG. 11 is a diagram showing arrangement of measured points according to the present invention.

FIG. 11 shows arrangement of measured points in the present invention.

In the case where measurement is effected while the focal spot is being switched over as described above, measured points are arranged in zigzags every projection data as represented by closed circles and open circles in FIG. 11. Since it is not necessary for the measuring system to satisfy the geometrical condition of expression (1) unlike the conventional interlacing method, a zigzag arrangement is obtained as a consequence. Therefore, the problem of design cost of the conventional technique is also solved.

In a data processing method according to the present invention, data on measured points arranged with a doubled density in a direction b as represented by ×in FIG. 11 are thus derived from data on measured points by interpolation processing in order to obtain a reconstructed image having a high resolution.

Details of this data processing will now be described by referring to FIG. 1. Data derived by measurement are subjected to necessary signal processing such as calibration and thereafter held in the memory 15 as projection data. Assuming that the number of projections is Na and the number of X-ray detector elements is Nb, this memory 15 must have a matrix size of at least Na×Nb.

In the interpolation calculating device 17, interpolation calculations are performed and projection data are generated with the number of projections of Na/2 and the number of X-ray detector elements of 2Nb. The projection data are written into the memory 16.

In order to hold all of the corrected projection data, the memory must have a matrix size of Na/2×2Nb. In the reconstruction calculation method such as the filtered backprojection method, however, it is not necessary to prepare all projection data at once. Therefore, corrected projection data of a necessary and sufficient amount may be successively transferred to a memory having a smaller size.

It is now assumed that projection data obtained by actual measurement and stored on the memory 15 is represented by P(i, j) using indexes i and j. This projection data P(i, j) means a value measured by a j-th X-ray detector element at the time of i-th projection (i=0, 1, ..., Na-1, j=0, 1, ..., Nb-1). On the other hand, corrected projection data held in the memory 16 is also represented by P'(i, j) likewise. As described before, the memory 16 does not always have a size of (Na/2×2Nb). At the time of a reconstruction calculation, however, each measured value is referred to by using i and j as indexes. Therefore, each measured value can be represented as P'(i, j) (i=0, 1, ..., Na/2-1, j=0, 1, ..., 2Nb-1).

If linear interpolation from three neighboring points, for example, is used as interpolation calculation, the correction data P'(i, j) is represented as in expression (2). At this time, weight G, index i0, and index j0 are functions of i, j and k, and they are calculated beforehand. Those calculated parameters are stored *in tables 18, 19 and 20 by using i, j and k as indexes and stored in data storage media such as read only memories or magnetic disks.

The interpolation calculator (double sampling data generator) 17 calculates the data P'(i, j) according to expression (2) while changing the indexes i and j.

$$P'(i,j) = \sum_{k=1}^{3} G(i,j,k)P(i0(i,j,k),j0(i,j,k)) \quad (2)$$

The weight G, index i0, and index j0 can be derived by calculating on the basis of information concerning arrangement of measured points, and are given as functions of i, j and k. Hereafter, the shift of positions of measured points consequent upon switchover of the focal spot position will be described.

Representing measured points of double sampling projection data as (a"(i, j), b"(i, j)) (i=0, 1, ..., Na/2-1, j=0, 1, ..., 2Nb-1), a" and b" are given by expression (3).

$$a"(i,j)=a_0+Da/2+i \cdot 2Da$$

$$b"(i,j)=b_0+j \cdot Db/2 \quad (3)$$

Figure 12:
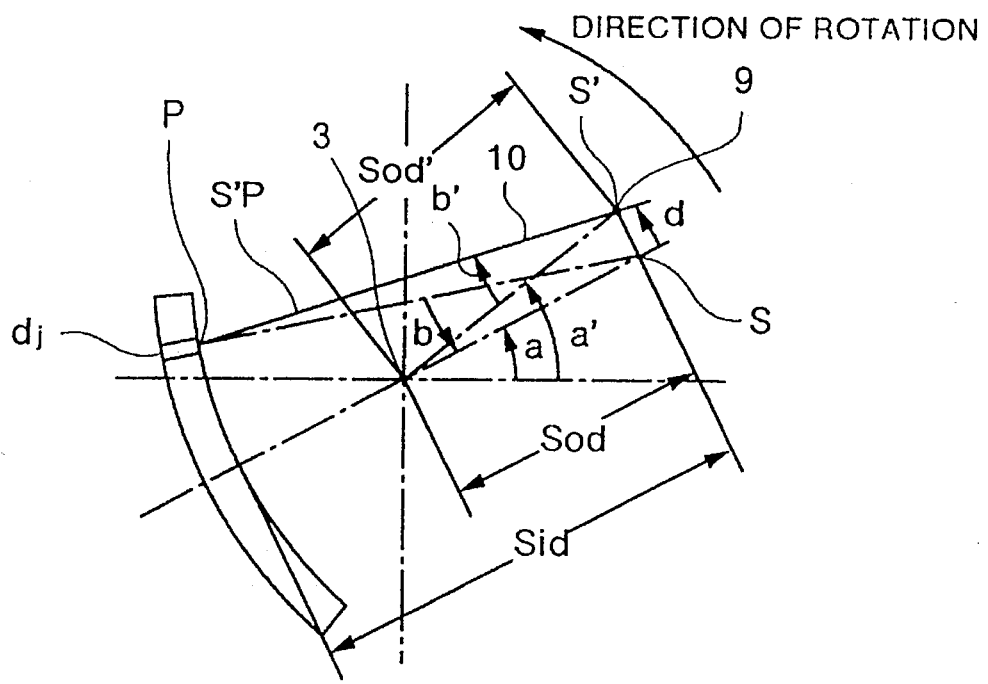
FIG. 12 is a diagram showing the geometric relation of a measuring system of an X-ray computed tomography apparatus according to the present invention.

FIG. 12 shows geometrical relations of the measuring system of the X-ray computed tomography apparatus according to the present invention.

In a projection with the X-ray source in a position (S) indicated by an angle a as shown in FIG. 12, an X-ray beam incident on an X-ray detector element dj located in a position indicated by an angle b will now be considered. If the X-ray focal spot is moved to the position S' located at a distance of d from the original position S, the X-ray beam incident on the X-ray detector element dj actually assumes an optical path indicated by a straight line S'P. At this time, a', b' and Sod' are calculated as functions of a, b and d by expressions (4), (5) and (6), respectively.

$$a'(a,b,d) = a + \tan^{-1}\frac{d}{Sod} \quad (4)$$

$$b'(a,b,d) = b + \tan^{-1}\frac{d \cdot Sid \cdot \cos b + Sod(Sid \cdot \sin b - d)}{Sod \cdot Sid \cdot \cos b - d(Sid \cdot \sin b - d)} \quad (5)$$

$$Sod'(a,b,d) = \sqrt{Sod^2 + d^2} \quad (6)$$

In an i-th (i=0, 1, ..., Na-1) projection counted from start of imaging, an X-ray beam incident on the j-th (j=0, 1, ..., Nb-1) X-ray detector element will now be considered. Assuming now that the original position of the X-ray source at this time is a(i, j) and the position of the X-ray detector element dj is b(i, j), they are represented by expression (7).

$$a(i,j)=a_0+i \cdot Da \quad b(i,j)=b_0+j \cdot Db \quad (7)$$

This $a_0$ is the position of the X-ray source at the time of start of measurement, and $b_0$ is the position of an X-ray detector element d0.

Since the position of the X-ray focal spot is switched over for data measurement of each projection, the shift d(i, j) of the X-ray focal spot is represented by expression (8).

$$d(i,j) = \begin{cases} +d (i = 0,2,4,...) \\ -d (i = 1,3,5,...) \end{cases} \quad (8)$$

By substituting expressions (7) and (8) into expressions (4) and (5), every (a', b') is derived as a function of i and j. That is to say, arrangement of all measured points is derived. Furthermore, it will be understood that arrangement of measured points can be controlled by controlling the shift of the X-ray focal spot.

A method for calculating the shift value of the X-ray focal spot required to obtain a high resolution image will now be described.

First of all, arrangement of measured points in projection i and arrangement of measured points in projection i+1 can be displaced by half of arrangement spacing of measured points by satisfying the condition of expression (9) (where n is a positive integer).

$$|b'(a,b,+d) - b'(a+Da,b,-d)| = (n+\tfrac{1}{2})Db \qquad (9)$$

Letting b=0 and substituting expression (5) into expression (9) yields expression (10). Solving expression (10) for d and letting d1 be the solution yields expression (11).

$$\left| 2\tan^{-1} \frac{d(Sid - Sod)}{Sod \cdot Sid + d^2} \right| = \left( n + \frac{1}{2} \right) Db \qquad (10)$$

$$d1 = \frac{(Sid - Sod) - \sqrt{(Sid - Sod)^2 - 4 Sid \cdot Sod \left( \tan \frac{(2n+1)Db}{4} \right)^2}}{2\tan \frac{(2n+1)Db}{4}} \qquad (11)$$

For arranging measured points of two adjacent projections on a single straight line in the b direction, it is necessary to satisfy expression (12). Substituting expression (4) into expression (12) yields expression (13). Solving expression (13) for d and letting d2 be the solution yields expression (14).

$$a'(a,b,+d) - a'(a + Da,b,-d) = 0 \qquad (12)$$

$$\tan^{-1} \frac{d}{Sod} = \frac{1}{2} Da \qquad (13)$$

$$d2 = Sod \cdot \tan \frac{Da}{2} \qquad (14)$$

In order that measured points of two adjacent projections are arranged on a single straight line and deviation of arranged measured points is a half of arrangement spacing as in the interlacing method, conditions of both expression (9) and expression (12) must be satisfied. Letting d3 be such a shift distance of the X-ray focal spot yields expression (15). If the shift distance d3 and geometrical parameters Sid, Sod, Da and Db of the measuring system satisfy expression (15), combining two adjacent projection data yields projection data having a doubled arrangement density in the b direction in the same way as the interlacing method. By reconstructing projection data thus combined, a high-resolution image can be obtained.

$$d3 = Sod \cdot \tan \frac{Da}{2} = \frac{(Sid - Sod) - \sqrt{(Sid - Sod)^2 - 4 Sid \cdot Sod \left( \tan \frac{(2n+1)Db}{4} \right)^2}}{2\tan \frac{(2n+1)Db}{4}} \qquad (15)$$

However, expression (15) places tough restrictions on geometrical relations of the measuring system. Such restrictions are equivalent to drawbacks of the interlacing method as already described and become restrictions on design of the apparatus.

If the condition that measured points of two adjacent projections must be arranged on a single straight line in the b direction is waived, it is necessary to satisfy the condition of expression (11) alone. Contents implied by expression (11) indicate that suitably setting only the shift distance of the X-ray focal spot on the geometrical setting of an existing measuring system displaces measured points of two adjacent projections by half a pitch.

A prime object of data processing in the present invention is to obtain projection data required to raise the resolution from arrangement of measured points obtained on the basis of this condition. That is to say, from two adjacent projection data, projection data having a doubled arrangement density in the b direction are derived by interpolation on the basis of arrangement of measured points. The projection data thus derived maintains the ideal arrangement pitch not only in the central part but also in the peripheral part. By reconstructing the double sampling projection data, a high-resolution image can be obtained.

By using not only two adjacent projection data but also more measured data, double sampling projection data may be derived by interpolation of a higher order.

Effects of the present invention can be described by roughly dividing into three parts.

A first effect resides in that a higher resolution of the reconstructed image can be achieved without limiting the flexibility on the design.

In the conventional interlacing method, relations as represented by expression (1) must subsist among the distance between the X-ray source and the center of rotation, the distance between the X-ray source and the X-ray detector elements, the rotation pitch of the scanner, the arrangement interval of the X-ray detector elements, and the shift distance of the X-ray focal spot. Because of this limitation, substantial redesign of the entire apparatus is needed to implement the interlacing method.

Meanwhile in the present invention, the shift distance of the X-ray focal spot can be derived on the basis of expression (11) for arbitrary values of the distance between the X-ray source and the center of rotation, the distance between the X-ray source and the X-ray detector elements, the rotation pitch of the scanner, and the arrangement interval of the X-ray detector elements. For implementing the present invention, therefore, it is not necessary to alter the geometric configuration of the apparatus and partial redesign of the conventional apparatus suffices. To the amount of absence of a substantial change in apparatus configuration, data processing is more complicated than the interlacing method. In fact, however, additional data processing is nothing but interpolation on a two-dimensional plane and it can be easily implemented.

A second effect resides in that projection data having an ideal sampling pitch can be obtained also in the peripheral part remote from the center of rotation.

In the conventional interlacing method, measured projection data are simply combined. In the peripheral part, therefore, a first projection and a second projection are not in the ideal interlaced relation and artifacts are caused on the reconstructed image. The present invention is able to solve this problem by conducting interpolation processing.

A third effect resides in that measurement satisfying the Nyquist condition can be effected without causing dead time and without lowering the time utilization efficiency on the premise that the conventional measured data transfer mechanism is used and consequently a high-resolution reconstructed image can be obtained.

If the data measuring system according to the present invention is used, timing for switching over the X-ray focal spot position can be set efficiently. Furthermore, measurement of projection data and transfer of measured data to the image reconstructor can be performed separately. Therefore, synchronization of measurement of projection data in all X-ray detector elements and successive transfer of measured data to the image reconstructor can be implemented efficiently without causing dead time. As a result, a high-resolution image free from artifacts can be obtained without lowering the signal-to-noise ratio.

Figure 13:
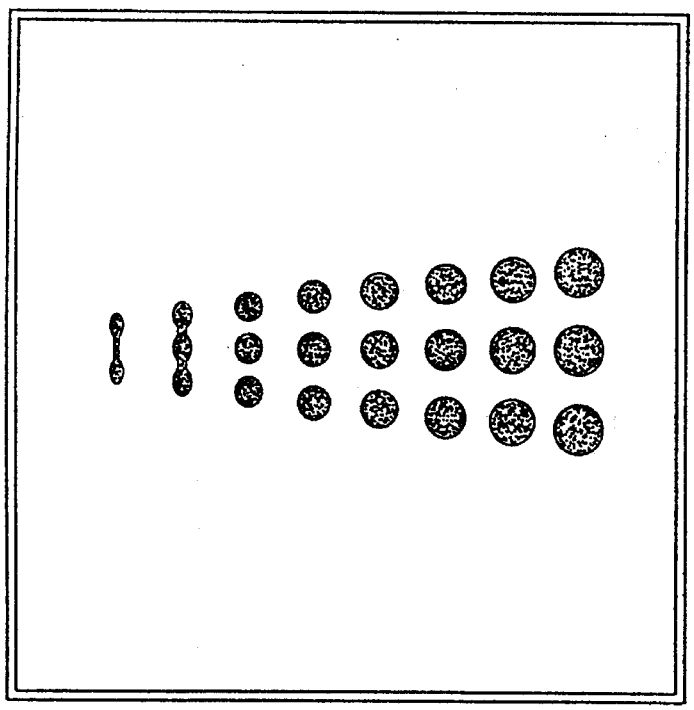
FIG. 13 is a diagram of a reconstructed image in the conventional method derived by computer simulation.
Figure 14:
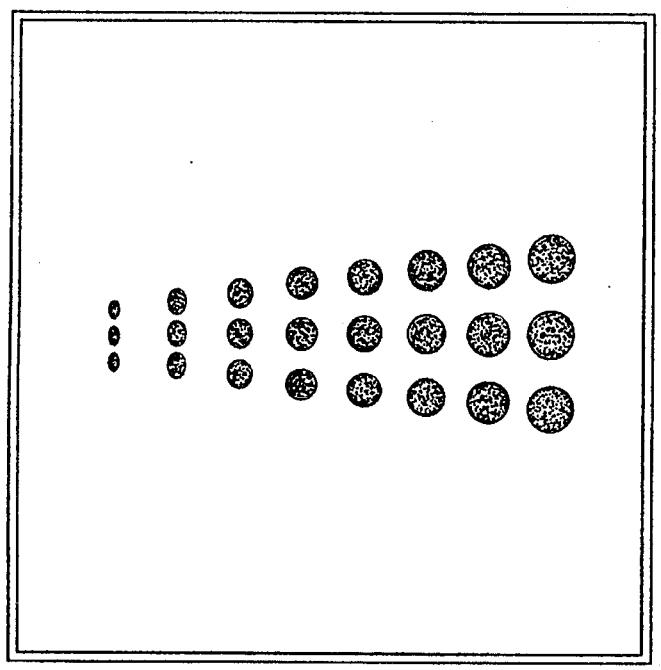
FIG. 14 is a diagram of a reconstructed image according to a present invention method derived by computer simulation.

FIG. 13 shows an image reconstructed by using the conventional method for the purpose of comparison. FIG. 14 shows an image reconstructed according to the present invention.

FIGS. 13 and 14 show results of computer simulation effected supposing a phantom having a contrast of 12% with respect to the background and including an X-ray absorbing substance with a diameter of 0.5 mm to 1.2 mm.

As for projection data obtained by applying the focal spot moving method according to the present invention, projection data having a doubled arrangement density in the b direction as a result of postprocessing were derived by interpolation. Comparing FIG. 13 with FIG. 14, it will be understood that while the X-ray absorbing substance having a diameter of 0.5 mm cannot be resolved by the conventional method, this can be resolved by the present invention method. Among a plurality of rows shown in FIGS. 13 and 14, the leftmost row corresponds to the X-ray absorbing substance of 0.5 mm.

Figure 15:
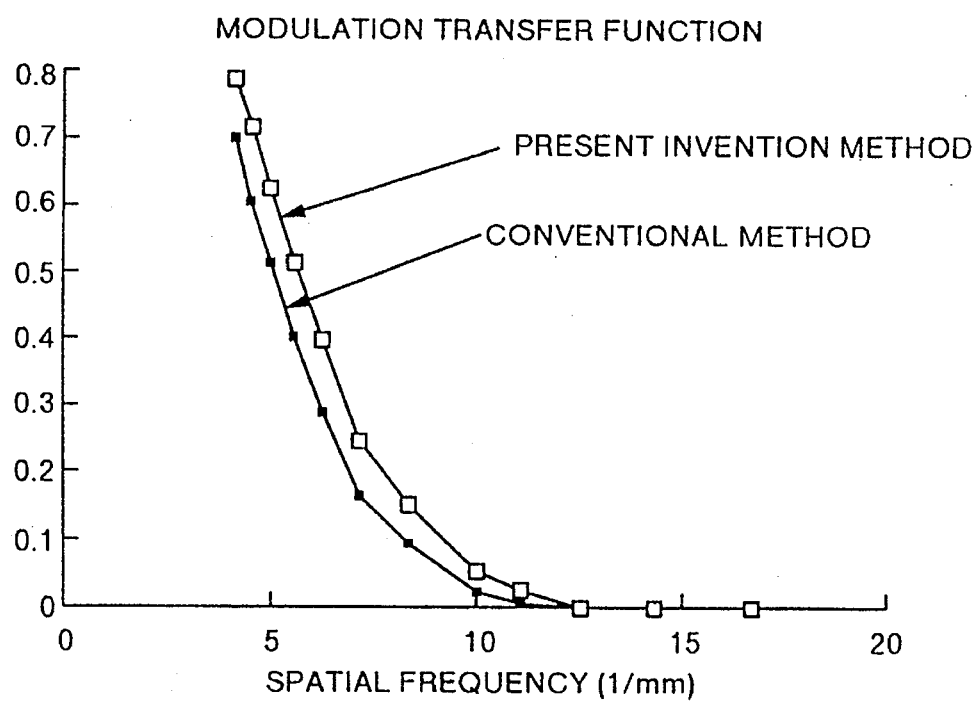
FIG. 15 is a characteristic diagram showing a modulation transfer function of the present invention method in comparison with a modulation transfer function of the conventional method.

FIG. 15 is a characteristic diagram showing a modulation transfer function of the conventional method derived by the computer simulation and a modulation transfer function of the present invention method derived by the computer simulation.

The modulation transfer function indicates the degree of modulation for each spatial frequency and provides one of methods for evaluating the resolution. The modulation transfer function having a value of unity means that the original X-ray absorption coefficient is correctly reproduced. The condition of the simulation is the same as that described before. As apparent from FIG. 15, reproducibility is better even at higher spatial frequencues in the present invention method than the conventional method. It will be understood that the present invention method is excellent in the aspect of resolution.

We claim:

1. An X-ray computed tomography apparatus for reconstructing a distribution of X-ray attenuation coefficient within an object on the basis of projection data derived from a plurality of directions, said X-ray computed tomography apparatus comprising:

an X-ray source for continuously generating X-rays to expose said object thereto;

an arrangement of a plurality of X-ray detector elements disposed on an opposite side of said X-ray source from said object, said X-ray detector elements being arranged with a predetermined arrangement pitch angle to measure X-rays transmitted through said object as projection data;

means for rotating positions of said X-ray source and said arrangement of X-ray detector elements by minute angles;

control means for shifting an X-ray focal spot position of said X-ray source;

a plurality of first temporary holding means respectively connected to said X-ray detector elements, a measured value of X-ray intensity transmitted through said object to be incident on one of said X-ray detector elements being temporarily held in one of said first temporary holding means;

switch means for switching over connection between said X-ray detector elements and said first temporary holding means;

switchover control means for controlling switchover of said switch means;

transfer means for transferring said measured value from said first temporary holding means to interpolation calculating means;

interpolation calculating means for performing interpolation calculations on said projection data including said measured value to generate projection data equivalent to projection data measured by using a measuring system virtually having twice as many X-ray detector elements as said arranged X-ray detector elements;

image reconstruction means for reconstrucing the distribution of X-ray attenuation coefficient within the object on the basis of the projection data generated by said interpolation calculating means; and a memory for holding parameters used for calculations in said interpolation calculating means.

2. An X-ray computed tomography apparatus according to claim 1, wherein said first temporary holding means comprises an integrator circuit supplied with incident X-ray intensity measured by one of said X-ray detector elements as an input, said integrator circuit integrating a value of said incident X-ray intensity for a fixed time.

3. An X-ray computed tomography apparatus according to claim 1, wherein said switchover control means controls said transfer means in response to switchover timing of said X-ray focal spot position and in accordance with order of arrangement of said X-ray detector elements.

4. An X-ray computed tomography apparatus according to claim 1, wherein said switchover control means controls on/off switchover of said switch means in response to switchover timing of said X-ray focal spot position.

5. An X-ray computed tomography apparatus for reconstructing a distribution of X-ray attenuation coefficient within an object on the basis of projection data derived from a plurality of directions, said X-ray computed tomography apparatus comprising:

an X-ray source for continuously generating X-rays to expose said object thereto;

an arrangement of a plurality of X-ray detector elements disposed on an opposite side of said X-ray source from said object, said X-ray detector elements being arranged with a predetermined arrangement pitch angle to measure X-rays transmitted through said object as projection data;

means for rotating positions of said X-ray source and said arrangement of X-ray detector elements by minute angles;

control means for shifting an X-ray focal spot position of said X-ray source;

first temporary holding means respectively connected to said X-ray detector elements to temporarily hold measured values of X-ray intensity transmitted through said object to be incident on said X-ray detector elements;

second temporary holding means respectively connected to said first temporary holding means via switch means to temporarily hold said measured values, respectively;

switchover control means for controlling on/off switchover of said switch means;

transfer means for transferring said measured values from said second temporary holding means to interpolation calculating means in order;

interpolation calculating means for performing interpolation calculations on said projection data including said measured values to generate projection data equivalent to projection data measured by using a measuring system virtually having twice as many X-ray detector elements as said arranged X-ray detector elements;

image reconstruction means for reconstructing the distribution of X-ray attenuation coefficient within the object on the basis of the projection data generated by said interpolation calculating means; and a memory for holding parameters used for calculations in said interpolation calculating means.

6. An X-ray computed tomography apparatus according to claim 5, wherein each of said first temporary holding means comprises an integrator circuit supplied with incident X-ray intensity measured by one of said X-ray detector elements as an input, said integrator circuit integrating a value of said incident X-ray intensity for a fixed time.

7. An X-ray computed tomography apparatus according to claim 5, wherein said switchover control means controls switchover of said switch means in response to switchover timing of said X-ray focal spot position.

8. An X-ray computed tomography apparatus according to claim 5, wherein said switchover control means controls on/off switchover of said switch means in response to switchover timing of said X-ray focal spot position.

9. An X-ray computed tomography apparatus according to claim 5, wherein said switchover control means controls said transfer means in accordance with order of arrangement of said X-ray detector elements.

10. An X-ray computed tomography method for reconstructing a distribution of X-ray attenuation coefficient within an object on the basis of projection data derived from a plurality of directions, said X-ray computed tomography method comprising the steps of:

continuously exposing said object to X-rays generated by said X-ray source;

measuring X-rays transmitted through said object as projection data by using an arrangement of a plurality of X-ray detector elements disposed on an opposite side of said X-ray source from said object, while rotating positions of said X-ray source and said arrangement of X-ray detector elements by minute angles, said X-ray detector elements being arranged with a predetermined arrangement pitch angle;

shifting an X-ray focal spot position of said X-ray source;

temporarily holding a measured value of X-ray intensity transmitted through said object to be incident on one of said X-ray detector elements in one of a plurality of first temporary holding means respectively connected to said X-ray detector elements;

switching over connection of switch means disposed between said X-ray detector elements and said first temporary holding means;

controlling switchover of said switch means;

transferring said measured value from said first temporary holding means to interpolation calculating means;

performing interpolation calculations on said projection data including said measured value to generate projection data equivalent to projection data measured by using a measuring system virtually having twice as many X-ray detector elements as said arranged X-ray detector elements; and reconstructing the distribution of X-ray attenuation coefficient within the object on the basis of the projection data generated by said interpolation calculatng means.

11. An X-ray computed tomography method for reconstructing a distribution of X-ray attenuation coefficient within an object on the basis of projection data derived from a plurality of directions, said X-ray computed tomography method comprising the steps of:

continuously exposing said object to X-rays generated by said X-ray source;

measuring X-rays transmitted through said object as projection data by using an arrangement of a plurality of X-ray detector elements disposed on an opposite side of said X-ray source from said object, while rotating positions of said X-ray source and said arrangement of X-ray detector elements by minute angles, said X-ray detector elements being arranged with a predetermined arrangement pitch angle;

shifting an X-ray focal spot position of said X-ray source;

temporarily holding measured values of X-ray intensity transmitted through said object to be incident on said X-ray detector elements in a plurality of first temporary holding means respectively connected to said X-ray detector elements;

switching over on/off of connection of switch means disposed between said first temporary holding means and second temporary holding means for temporarily holding said measured values, and controlling switchover of said switch means;

transferring said measured values from said second temporary holding means to image interpolation calculating means;

performing interpolation calculations on said projection data including said measured values to generate projection data equivalent to projection data measured by using a measuring system virtually having twice as many X-ray detector elements as said arranged X-ray detector elements; and reconstructing the distribution of X-ray attenuation coefficient within the object on the basis of the projection data generated by said interpolation calculating means.

12. An X-ray computed tomography method according to claim 10, wherein said temporary holding step comprises the step of integrating, for a fixed time, a value of incident X-ray intensity measured by said X-ray detector elements and supplied as an input.

13. An X-ray computed tomography method according to claim 10, wherein said controlling step comprises the step of controlling said transferring step in response to switchover timing of said X-ray focal spot position and in accordance with order of arrangement of said X-ray detector elements.

14. An X-ray computed tomography method according to claim 10, wherein said controlling step comprises the step of controlling on/off switchover of said switch means in response to switchover timing of said X-ray focal spot position.

15. An X-ray computed tomography method for reconstructing a distribution of X-ray attenuation coefficient within an object on the basis of projection data derived from a plurality of directions, said X-ray computed tomography method comprising the steps of:

continuously exposing said object to X-rays generated by said X-ray source;

measuring X-rays transmitted through said object as projection data by using an arrangement of a plurality of X-ray detector elements disposed on an opposite side of said X-ray source from said object, while rotating positions of said X-ray source and said arrangement of X-ray detector elements by minute angles (Da), said X-ray detector elements being arranged with a predetermined arrangement pitch angle (Db);

disposing an X-ray focal spot position of said X-ray source alternately in a first position and a second position;

temporarily holding a measured value of X-ray intensity transmitted through said object to be incident on one of said X-ray detector elements in one of a plurality of first temporary holding means respectively connected to said X-ray detector elements;

switching over connection of switch means disposed between said X-ray detector elements and said first temporary holding means, in response to timing of positioning or alteration of said X-ray focal spot position;

controlling switchover of said switch means; and transferring said measured value from said first temporary holding means to image reconstructor means.

16. An X-ray computed tomography method for reconstructing a distribution of X-ray attenuation coefficient within an object on the basis of projection data derived from a plurality of directions, said X-ray computed tomography method comprising the steps of:

continuously exposing said object to X-rays generated by said X-ray source;

measuring X-rays transmitted through said object as projection data by using an arrangement of a plurality of X-ray detector elements disposed on an opposite side of said X-ray source from said object, while rotating positions of said X-ray source and said arrangement of X-ray detector elements by minute angles (Da), said X-ray detector elements being arranged with a predetermined arrangement pitch angle (Db);

disposing an X-ray focal spot position of said X-ray source alternately in a first position and a second position;

temporarily holding measured values of X-ray intensity transmitted through said object to be incident on said X-ray detector elements in a plurality of first temporary holding means respectively connected to said X-ray detector elements;

switching over on/off of connection of switch means disposed between said first temporary holding means and second temporary holding means for temporarily holding said measured values, in response to timing of positioning or alteration of said X-ray focal spot position;

controlling switchover of said switch means; and transferring said measured values from said second temporary holding means to image reconstructor means in order.

17. An X-ray computed tomography method according to claim 15, further comprising the step of performing interpolation calculations on said projection data including said measured values to generate projection data equivalent to projection data measured by using a measuring system virtually having twice as many X-ray detector elements as said arranged X-ray detector elements.

18. An X-ray computed tomography method according to claim 17, wherein said interpolation calculation performing step comprises the step of correcting said projection data actually measured by referring to first values and second values respectively stored in memories and thereby deriving projection data corresponding to projection data obtained by said virtual measuring system, each of said first values being calculated beforehand from information concerning a position of said X-ray focal spot position and positions of said X-ray detector elements at the time of acquisition of each projection data actually measured, each of said second values being calculated beforehand from information concerning a position of said X-ray focal spot position and positions of said X-ray detector elements in each projection data obtained supposing measurement to be effected by said virtual measuring system.

19. An X-ray computed tomography method according to claim 17, wherein said first position of said X-ray focal spot is obtained by moving said X-ray focal spot from a predetermined position by a distance d1 in a tangential direction of rotation, said second position of said X-ray focal spot is obtained by moving said X-ray focal spot from said predetermined popsition by the same distance d1 in a direction opposite to said tangential direction of rotation, and said distance d1 is represented by $$d1 = \frac{(Sid - Sod) - \sqrt{(Sid - Sod)^2 - 4 Sid \cdot Sod \left(\tan \frac{(2n+1)Db}{4}\right)^2}}{2 \tan \frac{(2n+1)Db}{4}} \quad (a)$$

where Sod is a distance between the X-ray source and the center of rotation, Sid is a distance between the X-ray source and the X-ray detector elements, Db is an arrangement pitch angle of the X-ray detector elements, and n is a positive integer.

20. An X-ray computed tomography method according to claim 17, wherein when said first position of the X-ray focal spot is located in a position obtained by moving the X-ray focal spot from a predetermioned position by a distance d1' in a tangential direction of rotation and said second position of the X-ray focal spot is located in a position obtained by moving the X-ray focal spot from a predetermioned position by the same distance d1' in a direction opposite to said tangential direction of rotation, a distance Sod between the X-ray source and the center of rotation, a distance Sid between the X-ray source and the X-ray detector elements, a rotation angle Da of the scanner for each projection, and an arrangement pitch angle Db of the X-ray detector elements satisfy the relation $$d1' = Sod \cdot \tan \frac{Da}{2} = \frac{(Sid - Sod) - \sqrt{(Sid - Sod)^2 - 4 Sid \cdot Sod \left(\tan \frac{(2n+1)Db}{4}\right)^2}}{2 \tan \frac{(2n+1)Db}{4}} \quad (b)$$

assuming n is a positive integer.

21. An X-ray computed tomography method according to claim 17, wherein assuming that a position of the X-ray source is a, a position of an X-ray detector element in a row of the X-ray detector elements is b, and a position of the X-ray focal spot has been moved from a predetermined position by d in a tangential direction of rotation, a', b', a" and b" themselves calculated by using $$a'(a,b,d) = a + \tan^{-1} \frac{d}{Sod} \quad (c)$$

-continued $$b'(a,b,d) = b + \tan^{-1} \frac{d \cdot Sid \cdot \cos b + Sod(Sid \cdot \sin b - d)}{Sod \cdot Sid \cdot \cos b - d(Sid \cdot \sin b - d)} \quad (d)$$

$$a''(i,j) = a_0 + Da/2 + i \cdot 2Da \quad (e)$$

$$b''(i,j) = b_0 + j \cdot Db/2$$

or values derived from a', b', a" and b" by calculations are held in memories as information to be referenced to in said interpolation calculation performing step.

* * * * *